US012687532B2

(12) United States Patent
Lincoln et al.

(10) Patent No.: US 12,687,532 B2
(45) Date of Patent: Jul. 21, 2026

(54) GALVANICALLY ISOLATED GAS SENSING SYSTEM FOR AEROSPACE APPLICATIONS

(71) Applicant: Kidde Technologies, Inc., Wilson, NC (US)

(72) Inventors: David L. Lincoln, Cromwell, CT (US); Joseph V. Mantese, Ellington, CT (US); Tianli Zhu, Glastonbury, CT (US); Changmin Cao, Cork City (IE); Michael T. Gorski, Clinton, CT (US); Christopher C. Shovlin, Wethersfield, CT (US)

(73) Assignee: Kidde Technologies, Inc., Wilson, NC (US)

( * ) Notice: Subject to any disclaimer, the term of this patent is extended or adjusted under 35 U.S.C. 154(b) by 317 days.

(21) Appl. No.: 18/376,235

(22) Filed: Oct. 3, 2023

(65) Prior Publication Data

US 2025/0110095 A1     Apr. 3, 2025

(51) Int. Cl.
*G01N 33/00* (2006.01)
*B64D 37/32* (2006.01)
*B64D 45/00* (2006.01)
*G08B 21/16* (2006.01)
(Continued)

(52) U.S. Cl.
CPC ......... *G01N 33/0062* (2013.01); *B64D 45/00* (2013.01); *G01N 33/0075* (2013.01); *H02J 50/30* (2016.02)

(58) Field of Classification Search
CPC ........... G01N 33/0062; G01N 33/0075; G01N 33/005; G01N 33/0063; B64D 45/00; B64D 37/30; B64D 37/32; B64D 2045/009; H02J 50/30; G08B 21/16
See application file for complete search history.

(56) References Cited

U.S. PATENT DOCUMENTS

| | | | | |
|---|---|---|---|---|
| 4,088,986 A | * | 5/1978 | Boucher .............. | G08B 29/181 |
| | | | | 324/71.5 |
| 7,356,209 B2 | | 4/2008 | Delcher et al. | |
| 8,081,313 B2 | | 12/2011 | Lam et al. | |
| (Continued) | | | | |

FOREIGN PATENT DOCUMENTS

| | | | | | |
|---|---|---|---|---|---|
| CN | 116798196 A | * | 9/2023 | ............. | G08B 21/16 |
| NO | 159889 B | * | 11/1988 | ............. | G01N 27/12 |

OTHER PUBLICATIONS

Extended European Search Report for EP Application No. 24204541.7, dated Feb. 11, 2025, 8 pages.
(Continued)

*Primary Examiner* — Laura Martin
*Assistant Examiner* — Anthony W Megna Fuentes
(74) *Attorney, Agent, or Firm* — Kinney & Lange, P.A.

(57) ABSTRACT

An aircraft sensing system includes a power and communications module, a sensor module in optical communication with the power and communications module, the sensor module being disposed in an at least partially enclosed space within the aircraft, and at least one gas sensor in communication with the sensor module, the at least one gas sensor being disposed in the at least partially enclosed space. The at least one gas sensor is configured to sense at least one flammable gas species or non-flammable gas species, and the sensor module and the at least one gas sensor are galvanically isolated from the power and communications module.

16 Claims, 2 Drawing Sheets

(51) Int. Cl.
    *H02J 50/30*           (2016.01)
    *B64D 37/30*         (2006.01)

(56)               References Cited

U.S. PATENT DOCUMENTS

| 2017/0268974 | A1 | | 9/2017 | Brown et al. | |
| 2021/0409116 | A1 | * | 12/2021 | Krimmer | H04B 10/69 |
| 2023/0120640 | A1 | | 4/2023 | Silvestri et al. | |

OTHER PUBLICATIONS

Y. Chen, et al.. "Optically powered gas monitoring system using single-mode fibre for underground coal mines", from Int'l. Journal of Coal Science & Technology, (2022), 12 pages.

* cited by examiner

GALVANICALLY ISOLATED GAS SENSING SYSTEM FOR AEROSPACE APPLICATIONS

BACKGROUND

The present disclosure relates to sensors, and more particularly to galvanically isolated sensors.

Gas sensors, like other electronics for aerospace applications, typically transmit data and/or are powered through copper wiring. Unlike sensing of non-flammable gases (e.g., carbon dioxide), sensing of flammable gases (e.g., carbon monoxide, hydrogen, and other hydrocarbons) for aerospace applications requires galvanic isolation to remove possible ignition sources, which is crucial for aviation safety. Optical fibers are particularly well-suited for aerospace applications since they do not transmit electrical signals, and can also be smaller, lighter, resistant to electromagnetic and radio frequency interference, and more durable than copper wiring.

SUMMARY

An aircraft sensing system includes a power and communications module, a sensor module in optical communication with the power and communications module, the sensor module being disposed in an at least partially enclosed space within the aircraft, and at least one gas sensor in communication with the sensor module, the at least one gas sensor being disposed in the at least partially enclosed space. The at least one gas sensor is configured to sense at least one flammable gas species or non-flammable gas species, and the sensor module and the at least one gas sensor are galvanically isolated from the power and communications module.

A method of monitoring a gas species on an aircraft includes sending, via a power and communications module, an optical power signal to a sensor module, powering, via the sensor module, at least one gas sensor, and sensing, via the at least one gas sensor, the gas species with an at least partially enclosed space aboard the aircraft. The gas species is a flammable gas species or a non-flammable gas species.

Figure 1:
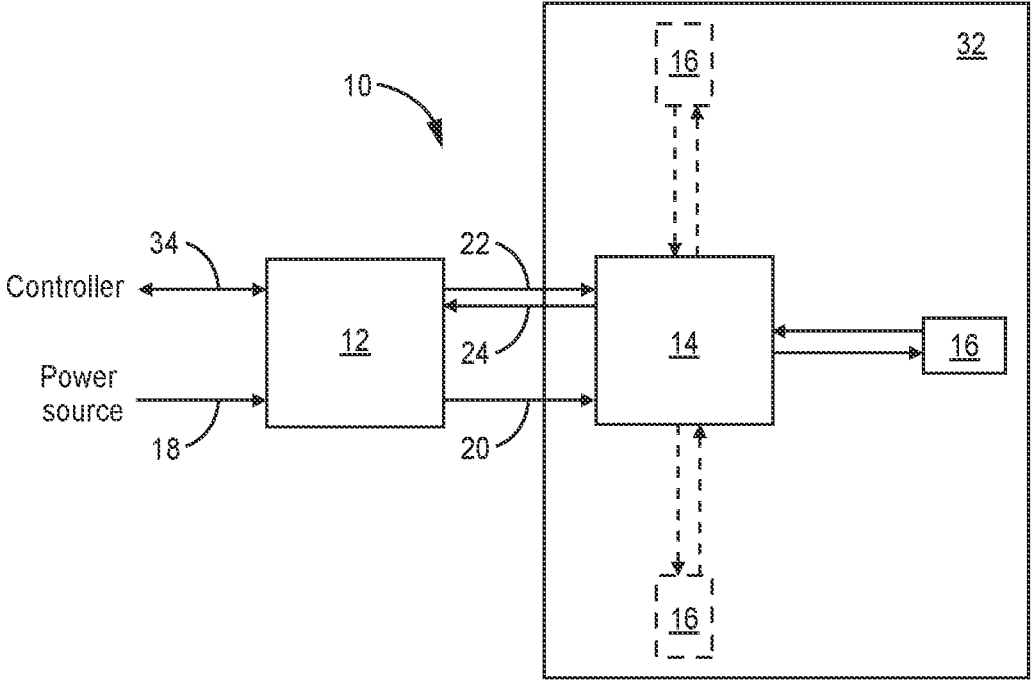
FIG. 1 is a schematic illustration of a gas sensing system for an aircraft.

While the above-identified figures set forth one or more embodiments of the present disclosure, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale, and applications and embodiments of the present invention may include features and components not specifically shown in the drawings.

DETAILED DESCRIPTION

This disclosure presents galvanically isolated sensor systems for sensing flammable and/or otherwise harmful gases. The gas sensors can preferably be used in aerospace applications, as is described below, although they can also be used in other vehicles and stationary structures.

Figure 2:
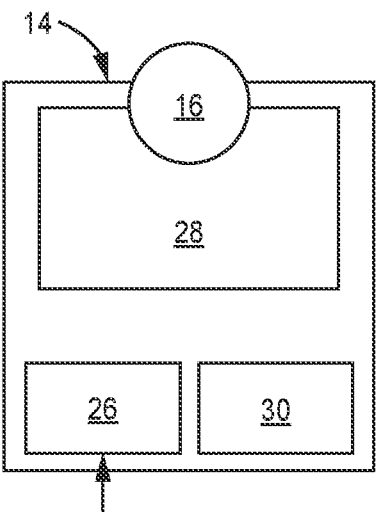
FIG. 2 is a schematic illustration of a sensor module and sensor belonging to the gas sensing system of FIG. 1.

FIG. 1 is a schematic illustration of sensing system 10. FIG. 2 is a schematic illustration of sensor module 14 and sensor 16 of system 10. FIGS. 1 and 2 are discussed together.

System 10 can include power and communications module (PCM) 12, sensor module (SM) 14, and at least one sensor 16. As shown in FIG. 1, system 10 includes optional second and third sensors 16, and can generally include 1 to n sensors, as limited by spatial constraints, power requirements, etc. PCM 12 can be used to power sensor 16 by converting electrical power from a power source (e.g., an aircraft battery) received via input line 18. The power source can provide, in some embodiments, 12 volts, 24 volts, or 48 volts of DC power to PCM 12. In an alternative embodiment, the power source can instead be a source of AC power. PCM 12 converts the voltage into an optical signal (e.g., as a laser) which can be provided to SM 14 via optical power line 20. Transceiver (TX) line 22 and receiver (RX) line 24 allow PCM 12 to bidirectionally communicate with SM 14, that is transmitting and receiving, respectively, data signals to/from SM 14. Accordingly, lines 20, 22, and 24 can all be fiber optic cables transmitting optical, and non-electrical signals. In an alternative embodiment, TX line 22 and RX line 24 can be incorporated into a single RX/TX line, instead of two distinct lines. In yet another alternative embodiment, the functions of lines 20, 22, and 24 can all be carried out by a single fiber optic cable configured for both power and data transmission.

SM 14 can include power converter 26 to convert the optical power signal back to an electrical signal to power any associated sensors 16. In this regard, SM 14 provides voltage isolated regulated power to sensor 16. In one embodiment, power converter 26 can be a photovoltaic cell. As shown in FIG. 2, sensor 16 can be collocated with SM 14, and in some embodiments, mounted on SM 14. SM 14 can further include signal conditioner 28 for formatting sensor 16 signals to be read/converted by analog-to-digital converter (ADC) 30 of SM 14.

Sensor 16 can be configured to sense/detect at least one gas species, including flammable species, such as hydrogen ($H_2$), carbon monoxide (CO), and other hydrocarbon gases within an at least partially enclosed space 32 of an aircraft. Space 32 can be, for example a cargo bay, the ullage space of a fuel tank, and/or proximate a fuel nozzle within the aircraft's engine. System 32 is configured such electrical power is not transmitted through space 32, rather, PCM 12 is disposed elsewhere on the aircraft (i.e., outside of space 32). Stated another way, SM 14 and sensor(s) 16 are galvanically isolated from the rest of system 10, receiving power only optically, and non-electrically from PCM 12. Sensor 16 can additionally and/or alternatively be configured to sense non-flammable, toxic species, or asphyxiant species, such as carbon dioxide ($CO_2$). As such, space 32 can further include a cabin or cockpit, where people might be present. Sensor 16 can be an electrochemical, metal oxide, catalytic bead, or optical sensor, depending on the sensing requirements. For example, electrochemical, metal oxide, and catalytic bead sensing modalities can all be used for hydrogen sensing. Sensor 16 can be a relatively low power sensor, with electrochemical modalities requiring only milliwatts of power, and the other modalities requiring watts. Sensed information can be conditioned then converted by signal conditioner 28 and ADC 30, and can be sent to PCM 12 via RX line 24. PCM 12 can communicate sensed data to the aircraft control system or other controller via universal serial bus (USB) or controller area network (CAN) bus 34.

In an alternative embodiment with multiple sensors 16, each sensor 16 can be collocated with its own SM 14, or with a common SM 14 as schematically represented in FIG. 1. More specifically, if system 10 includes multiple sensors 16 in close proximity to one another, a single SM 14 can support the multiple sensors 16. If multiple sensors 16 are instead disposed relatively far apart from one another, a corresponding number of SMs 14 may be preferable. Each sensor can be located in a single space 32 (e.g., a cargo bay), or each in a distinct space 32 (e.g., one sensor 16 in a fuel tank and another sensor 16 in a cargo bay). Additionally, each sensor 16 can be configured to sense a different gaseous species, as is discussed in greater detail below. Multiple sensors 16 can be connected in series or in parallel with PCM 12.

The alarm threshold of system 10 can vary depending on, for example, the gaseous species being detected. In an exemplary embodiment, sensor 16 can be configured to sense hydrogen, the lower flammability limit of which is 4% in air. In such an embodiment, system 10 can alarm when hydrogen concentrations in space 32, as sensed by sensor(s) 16, reach 1%, 2%, or somewhere therebetween (e.g., 1.5%). For non-flammable gases, a critical concentration can be used as the alarm threshold. System 10 can additionally and/or alternatively be configured to alarm based on a rate of change (i.e., rate of rise) in hydrogen concentrations in space 32 over a predetermined period of time. For example, an alarm threshold can be reached if the hydrogen concentration changes by a predetermined amount (e.g., 1%) and/or reaches a predetermined concentration (e.g., 2%) within a predetermined period of time ranging from 1 second to 300 seconds. Finally, the alarm threshold can vary depending on the type of space 32 being monitored and/or flight phase, as the presence of flammable or toxic species may not indicate an emergency situation when an aircraft is on the ground. To reduce the occurrence of false alarms caused by, for example, interference from other gases, system 10 can be configured such that two sensors 16 (e.g., hydrogen sensors) in space 32 must detect an alarmable amount of the gaseous species (e.g., 1% or 2% hydrogen) for system 10 to alarm. In some embodiments, two sensors 16 can have different sensing modalities (e.g., electrochemical and catalytic bead) while being configured to sense the same species (e.g., hydrogen). System 10 can trigger an audible and/or visual alarm in the cockpit.

For multi-gas sensing applications, system 10 can be variously configured. In one example, each sensor 16 can sense a different gaseous species, for example, with one sensor 16 sensing hydrogen and another sensor 16 sensing carbon monoxide in space 32. Alternatively, a single sensor 16 can be configured to sense and alarm for multiple gases, for example, at least two of carbon monoxide, carbon dioxide, and hydrogen sulfide ($H_2S$). In either example, system 10 can be configured with different alarm thresholds and/or rates of rise for each gaseous species being detected.

The disclosed sensing systems with galvanically isolated gas sensors allow for the necessary detection of flammable and/or toxic gaseous species in aircraft spaces while minimizing the risk of combustion in these aircraft spaces from electrical current.

Discussion of Possible Embodiments

The following are non-exclusive descriptions of possible embodiments of the present invention.

An aircraft sensing system includes a power and communications module, a sensor module in optical communication with the power and communications module, the sensor module being disposed in an at least partially enclosed space within the aircraft, and at least one gas sensor in communication with the sensor module, the at least one gas sensor being disposed in the at least partially enclosed space. The at least one gas sensor is configured to sense at least one flammable gas species or non-flammable gas species, and the sensor module and the at least one gas sensor are galvanically isolated from the power and communications module.

The system of the preceding paragraph can optionally include, additionally and/or alternatively, any one or more of the following features, configurations and/or additional components:

In the above system, the power and communications module can be in communication with a power source configured to supply electrical power to the power and communications module.

In any of the above systems, the power and communications module can be configured to convert the electrical power to an optical power signal.

In any of the above systems, the power and communications module can be configured to supply the optical power signal to the sensor module via a first fiber optic cable.

In any of the above systems, the power and communications module can be configured to bidirectionally communicate with the sensor module via at least one fiber optic cable.

In any of the above systems, the sensor module can include a photovoltaic power converter for converting the optical power signal to an electrical power signal to power the at least one sensor.

In any of the above systems, the sensor module can further include a signal conditioner, and an analog-to-digital converter.

In any of the above systems, the at least one flammable gas species can be at least one of hydrogen, carbon monoxide, and a hydrocarbon gas.

In any of the above systems, the at least one non-flammable gas species can be carbon dioxide.

In any of the above systems, the at least one gas sensor can be one of an electrochemical sensor, metal oxide sensor, catalytic bead sensor, and optical sensor.

In any of the above systems, the at least one gas sensor can include a first gas sensor and a second gas sensor.

In any of the above systems, the first gas sensor can be configured to sense a first flammable gas species, and the second gas sensor can be configured to sense a second flammable gas species different from the first flammable gas species.

In any of the above systems, the at least partially enclosed space can be one of a cargo bay, a fuel tank, a gas turbine engine, a cabin, and a cockpit.

In any of the above systems, the power and communications module can be located outside of the at least partially enclosed space.

In any of the above systems, the system can be configured to alarm when the at least one flammable gas species or toxic gas species reaches a threshold concentration.

In any of the above systems, the system can be configured to alarm when a concentration of the at least one flammable gas species or non-flammable gas species changes at a predetermined rate.

In any of the above systems, the sensor module can receive only optical signals from the power and communications module.

A method of monitoring a gas species on an aircraft includes sending, via a power and communications module, an optical power signal to a sensor module, powering, via the sensor module, at least one gas sensor, and sensing, via the at least one gas sensor, the gas species with an at least partially enclosed space aboard the aircraft. The gas species is a flammable gas species or a non-flammable gas species.

The method of the preceding paragraph can optionally include, additionally and/or alternatively, any one or more of the following features, configurations and/or additional steps:

The above method can further include triggering an alarm when the gas species sensed by the at least one gas sensor reaches a threshold concentration.

In any of the above methods, the gas species can be hydrogen, and the threshold concentration can be below a lower flammability limit of hydrogen.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. An aircraft sensing system comprising:
a power and communications module;
a sensor module in optical communication with the power and communications module, the sensor module being disposed in an at least partially enclosed space within the aircraft;
a first gas sensor in communication with the sensor module via a first fiber optic line, the first gas sensor being disposed in the at least partially enclosed space; and
a second gas sensor in communication with the sensor module via a second fiber optic line, the second gas sensor being disposed in the at least partially enclosed space,
wherein the sensor module is configured to condition signals from each of the first and second gas sensors, and to provide voltage isolated regulated power to each of the first and second gas sensors;
wherein the sensor module is configured to intake non-electrical signals from the first fiber optic line and the second fiber optic line, and send an output signal to the power and communications module via optical communication via a single communication fiber optic line; and
wherein the sensor module, the first gas sensor, and the second gas sensor are galvanically isolated from the power and communications module.

2. The system of claim 1, wherein the power and communications module is in communication with a power source configured to supply electrical power to the power and communications module.

3. The system of claim 2, wherein the power and communications module is configured to convert the electrical power to an optical power signal.

4. The system of claim 3, wherein the power and communications module is configured to supply the optical power signal to the sensor module via a first fiber optic cable.

5. The system of claim 4, wherein the power and communications module is configured to bidirectionally communicate with the sensor module via at least one fiber optic cable.

6. The system of claim 3, wherein the sensor module comprises a photovoltaic power converter for converting the optical power signal to an electrical power signal to power the at least one sensor.

7. The system of claim 1, wherein the sensor module further comprises:
a signal conditioner; and
an analog-to-digital converter.

8. The system of claim 1, wherein the first and second gas sensors are one of an electrochemical sensor, metal oxide sensor, catalytic bead sensor, and optical sensor.

9. The system of claim 1, wherein the at least partially enclosed space is one of a cargo bay, a fuel tank, a gas turbine engine, a cabin, and a cockpit.

10. The system of claim 9, wherein the power and communications module is located outside of the at least partially enclosed space.

11. The system of claim 1, wherein the sensor module receives only optical signals from the power and communications module.

12. The system of claim 1, wherein the first gas sensor is configured to sense a first flammable gas species, and wherein the second gas sensor is configured to sense multiple flammable gas species, all of the multiple flammable gas species different from the first flammable gas species.

13. The system of claim 12, wherein the first flammable gas species is at least one of hydrogen, carbon monoxide, and a hydrocarbon gas.

14. The system of claim 12, wherein the system is configured to alarm when the first flammable gas species or toxic gas species reaches a threshold concentration.

15. The system of claim 12, wherein the system is configured to alarm when a concentration of the first flammable gas species changes at a predetermined rate.

16. The system of claim 1, wherein the sensor module is in optical communication with the power and communications module via an optical power line, an optical signal transmission line, and an optical signal receiver line.

* * * * *